Figure 1:
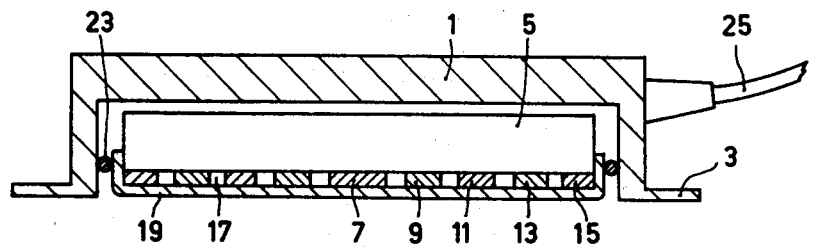

United States Patent [19]

Albarda et al.

[11] 4,324,257
[45] Apr. 13, 1982

[54] DEVICE FOR THE TRANSCUTANEOUS MEASUREMENT OF THE PARTIAL OXYGEN PRESSURE IN BLOOD

[75] Inventors: Scato Albarda, Lübeck, Fed. Rep. of Germany; Martinus H. Kuijpers, Eindhoven, Netherlands

[73] Assignee: U.S. Philips Corporation, New York, N.Y.

[21] Appl. No.: 124,405

[22] Filed: Feb. 25, 1980

Related U.S. Application Data

[63] Continuation of Ser. No. 8,137, Jan. 31, 1979, abandoned.

[30] Foreign Application Priority Data

Feb. 20, 1978 [NL] Netherlands ..................... 7801867

[51] Int. Cl.$^3$ .................................................... A61B 5/00
[52] U.S. Cl. ........................... 128/635; 204/195 B
[58] Field of Search .......................... 128/635, 639; 204/195 B, 195 P

[56] References Cited

U.S. PATENT DOCUMENTS

| | | | |
|---|---|---|---|
| 3,000,805 | 9/1961 | Carritt et al. | 128/635 |
| 3,454,485 | 7/1969 | Hauk et al. | 204/195 P |
| 3,787,308 | 1/1974 | Malaspina et al. | 204/195 P |
| 3,868,947 | 3/1975 | Holsinger | 128/639 |
| 3,985,633 | 10/1976 | Lubbers et al. | 128/635 |
| 4,176,659 | 12/1977 | Rolfe | 204/195 B |

*Primary Examiner*—William E. Kamm
*Attorney, Agent, or Firm*—Thomas A. Briody; Robert T. Mayer; Jack E. Haken

[57] ABSTRACT

A device for the transcutaneous measurement of the partial oxygen pressure in blood, comprising a measuring head which includes a measuring cell of the Clark-type which is surrounded by one or more annular shielding cells of the Clark-type in order to eliminate any oxygen which laterally penetrates from the ambient air.

6 Claims, 2 Drawing Figures

U.S. Patent  Apr. 13, 1982  4,324,257

DEVICE FOR THE TRANSCUTANEOUS MEASUREMENT OF THE PARTIAL OXYGEN PRESSURE IN BLOOD

This is a continuation of application Ser. No. 008,137, filed Jan. 31, 1979, now abandoned.

The invention relates to a device for the transcutaneous measurement of the partial oxygen pressure in the blood of humans or animals, comprising a measuring head which is to be arranged on the skin and which comprises at least one measuring cell which is connected to an ammeter and which comprises at least one measuring electrode and one reference electrode, said electrodes being accommodated in a space which contains an electrolyte solution, one wall thereof which faces the skin in the operating condition being formed by an oxygen-permeable diaphragm.

A device of this kind is known from German Auslegeschrift No. 2,255,879. In this known device, the actual measuring cell is enclosed by a groove which can be connected to a vacuum pump in order to suck the measuring head down onto the skin. This step is taken to reduce the risk of leakage of oxygen from the air between the edge of the measuring head and the skin. Leakage of this kind would cause the partial oxygen pressure at the area of the measuring cell to be higher than the oxygen pressure caused by the diffusion of oxygen from the peripheral blood vessels through the skin to the measuring cell.

In practice, it has been found that the known device does not provide absolute certainty against the ingress of oxygen from the air and, moreover, the connection of the measuring head to a vacuum pump is expensive and annoying to the patient.

The invention has for its object to provide a device of the described kind in which the said drawbacks are eliminated. To this end, the device in accordance with the invention is characterized in that the measuring cell is surrounded by an essentially annular second measuring electrode and an essentially annular second reference electrode which are situated in a space similar to that in which the electrodes of the measuring cell are situated and which form part of a shielding cell which surrounds the measuring cell.

The shielding cell consumes any oxygen entering by leakage, so that this oxygen cannot reach the measuring cell.

An embodiment of the device in accordance with the invention, having a compact construction, is characterized in that the measuring cell and the shielding cell have a common space which is filled with electrolyte solution.

A further preferred embodiment of the device in accordance with the invention is characterized in that a second, also essentially annular shielding cell is situated between the shielding cell and the measuring cell, said second shielding cell being connected, like the measuring cell, to an ammeter.

The inner shielding cell can as yet consume any oxygen from the air which is not consumed by the outer shielding cell. Moreover, the current through the inner shielding cell is a measure for the quantity of oxygen passing the outer shielding cell. As a result, the inner shielding cell gives an indication as regards the presence of any major leaks.

The invention will be described in detail hereinafter with reference to the accompanying diagrammatic drawing.

Figure 2:
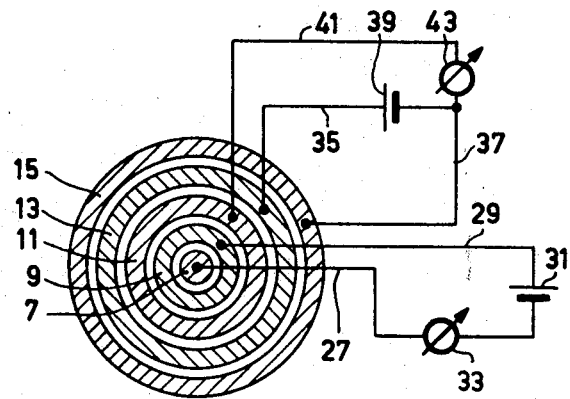

FIG. 1 is a cross-sectional view of an embodiment of a measuring head for a device in accordance with the invention, and FIG. 2 shows a diagram of the circuit of a device comprising the measuring head shown in FIG. 1.

The measuring head shown in FIG. 1 comprises a cylindrical metal housing 1 which is provided with a flange 3 which can be arranged on the skin and which can be secured thereto by means of an adhesive strip. In the housing 1 there is accommodated an insulating body 5, for example, of glass or a synthetic material, on the lower side of which there are provided a number of electrodes by way of a known technique as used for the deposition of this metal layers. The electrodes form a concentric pattern, a first measuring electrode 7 being situated in the centre and a number of annular electrodes being successively situated around this first electrode: a first reference electrode 9, a second measuring electrode 11, a second reference electrode 13, and a third measuring electrode 15. The reference electrodes are made of chlorated silver and the measuring electrodes are made of platinum or gold.

The electrodes are situated in a space 17 which is filled with an electrolyte solution, preferably KCl. The wall of the space 17 which faces the skin in the operating condition is formed by an oxygen-permeable diaphragm 19 of, for example, polytetrafluoroethylene, which is clamped against the body 5 in a liquid-tight manner by way of a clamping ring 23.

Each of the electrodes is connected, via a conductor, (not visible in FIG. 1), which is embedded, for example in the body 5, to one of the cores of a connection cable 25 which connects the measuring head to further parts of the device. As appear from FIG. 2, the first measuring electrode 7 and the first reference electrode 9 are connected, via conductors 27 and 29, respectively, to a d.c. voltage source 31 and a first ammeter 33. These electrodes form part of a measuring cell which produces an electrical current which is to be recorded by the ammeter 33 and which is proportional to the partial oxygen pressure at the area of the centre of the diaphragm 19. The measuring cell consumes oxygen which is replenished by diffusion of oxygen from the subcutaneous peripheral blood vessels.

In order to prevent oxygen which penetrates from the air, between the flange 3 and the skin, from influencing the measuring cell, the electrodes 11, 13 and 15 form part of two shielding cells. The outer shielding cell contains the electrodes 13 and 15 which are connected, via conductors 35 and 37, respectively, to a d.c. voltage source 39. The inner shielding cell has the second reference electrode 13 in common with the outer shielding cell. It furthermore contains the second measuring electrode 11 which is also connected, via a conductor 41 and a second ammeter 43, to the d.c. voltage source 39.

Oxygen penetrating between the flange 3 and the skin or via the epidermis underneath the flange, is consumed mainly by the first shielding cell. The remainder, passing the first shielding cell, is consumed by the second shielding cell, the second ammeter 43 indicating the extent of this remainder. An excessive value of the current indicated by this meter signifies a major leak which may be caused, for example, in that the adhesive strip whereby the measuring head is secured to the skin locally does not properly adhere.

Obviously, if desired, each of the two shielding cells may be provided with its own set of electrodes. The use of a common reference electrode 13, however, saves space and costs. Instead of the reference electrode, the measuring electrode may also be common to both shielding cells. It is also possible to construct one or both shielding cells as a separate annular construction which is arranged around a standard measuring cell.

The described construction of the measuring cell and the shielding cells is given merely by way of example. Other examples of the construction of such cells (so-termed Clark-cells) are described inter alia in German Auslegeschrift No. 2,255,879, French Pat. No. 2,245,248 and Netherlands Pat. No. 152,084. If necessary, a plurality of measuring cells may be surrounded by a common shielding cell.

The ammeters 33 and 43 may consist of simple dial instruments or of circuits which control, for example, a recording instrument.

What is claimed is:

1. A device for the transcutaneous measurement of partial oxygen pressure in the blood of humans or animals, comprising:
    a measuring head;
    a measuring cell contained in a space within said measuring head which includes a first measuring electrode, a first reference electrode, and an electrolyte solution surrounding said first electrodes; oxygen permeable diaphragm means disposed between said first electrodes and the skin which function to contain the solution within said space; and
    a essentially annular shielding cell which surrounds the measuring cell and includes an essentially annular second measuring electrode and an essentially annular second reference electrode; said second electrodes being situated in a space within said measuring head which is similar to the space containing the measuring cell.

2. A device as claimed in claim 1 wherein the measuring cell and the shielding cell are contained within a single common space in the measuring head, which space is filled with said electrolyte solution.

3. A device as claimed in claim 1 or 2 further comprising a second essentially annular shielding cell disposed between said measuring cell and said first shielding cell.

4. A device as claimed in claim 3 wherein the first shielding cell and the second shielding cell comprise a single common electrode.

5. A device as claimed in claim 1 further comprising an ammeter connected to measure current flow in the measuring cell.

6. A device as claimed in claim 3 further comprising a first ammeter connected to measure current in the measuring cell and a second ammeter connected to measure current in the second shielding cell.

* * * * *